United States Patent [19]
Valentine et al.

[11] Patent Number: 5,501,714
[45] Date of Patent: Mar. 26, 1996

[54] OPERATION OF DIESEL ENGINES WITH REDUCED PARTICULATE EMISSION BY UTILIZATION OF PLATINUM GROUP METAL FUEL ADDITIVE AND PASS-THROUGH CATALYTIC OXIDIZER

[75] Inventors: James M. Valentine, Fairfield, Conn.; Jeremy D. Peter-Hoblyn, Bodwin, England

[73] Assignee: Platinum Plus, Inc., Stamford, Conn.

[21] Appl. No.: 403,365

[22] Filed: Mar. 14, 1995

Related U.S. Application Data

[63] Continuation-in-part of Ser. No. 372,188, Jan. 13, 1995, which is a continuation-in-part of Ser. No. 251,520, May 31, 1994, which is a continuation-in-part of Ser. No. 918,679, Jul. 22, 1992, abandoned, and a continuation-in-part of Ser. No. 251,520, May 31, 1994, abandoned, which is a continuation-in-part of Ser. No. 918,679, Jul. 22, 1992, abandoned, and a continuation-in-part of Ser. No. 3,245, Jan. 11, 1993, abandoned, which is a continuation-in-part of Ser. No. 808,435, Dec. 16, 1991, abandoned, which is a continuation-in-part of Ser. No. 794,329, Nov. 12, 1991, abandoned, which is a continuation of Ser. No. 291,245, Dec. 28, 1988, abandoned.

[51] Int. Cl.$^6$ .................................................. C10L 1/30
[52] U.S. Cl. .................. 44/358; 44/361; 44/359; 44/363; 44/364
[58] Field of Search .................. 44/355, 358, 359, 44/361, 363, 364

[56] References Cited

U.S. PATENT DOCUMENTS

| | | | |
|---|---|---|---|
| 4,475,483 | 10/1984 | Robinson | 44/359 |
| 4,629,472 | 12/1986 | Haney et al. | 44/51 |
| 4,891,050 | 1/1990 | Bowers et al. | 44/67 |
| 4,892,562 | 1/1990 | Bowers et al. | 44/67 |
| 5,034,020 | 7/1991 | Epperly et al. | 44/358 |
| 5,216,875 | 6/1993 | Kennelly et al. | 60/39.02 |
| 5,258,349 | 11/1993 | Dalla Betta et al. | 502/330 |
| 5,266,083 | 11/1993 | Peter-Hoblyn et al. | 44/358 |
| 5,279,627 | 1/1994 | Huang et al. | 44/358 |

OTHER PUBLICATIONS

Beckmann, R., et al., "A New Generation of Diesel Oxidation Catalysts", SAE Technical Paper Series No. 922330, San Francisco, CA, Oct. 19–22, 1992.

Bertelsen, Bruce I., "Particulate Emission Control of Diesel Fueled Vehicles", Manufacturers of Emission Controls Assn., Washington, DC, Jul. 1994.

McCabe, R. W. et al., "Oxidation of Diesel Particulates by Catalyzed Wall–Flow Monolith Filters. 2 Regeneration Characteristics of Platinum, Lithium, and Platinum–Lithium Catalyzed Filters", SAE Technical Papers Series 872137, Toronto, Canada.

Snider, S., et al., "Control of Diesel Engine Exhaust Emissions in Underground Mining", 2nd US Mine Ventilation Symposium, Reno, Nevada, Sep. 23–25, 1985.

Heinrich, U., et al., "Tierexperimentelle Inhalationsstudien Zur Frage der Tumorinduzierenden Wirkung von Dieselmotorabgasen und Zwei Teststauben", Oklologische Forchung BMFT/GSF, Munich, 1992 month unavailable.

Primary Examiner—Jacqueline V. Howard
Attorney, Agent, or Firm—St. Onge, Steward Johnston & Reens

[57] ABSTRACT

The invention provides a method employing a fuel additive to improve the operation of a pass-through oxidation catalyst over long periods of time with continued catalytic activity and without the undesirable conversion of $SO_2$ to $SO_3$. A pass-through catalyst support is continuously, selectively catalyzed by the combustion of a fuel containing a platinum group metal composition which burns to release the catalyst metal in active form. The effectiveness of the process is attributed to improved combustion in the engine by the catalyst and the treatment of the catalytic oxidizer with active catalyst metal released during combustion such that, in the exhaust system, the soluble organic fraction of the particulates and the levels of gaseous unburned hydrocarbons and carbon monoxide are significantly reduced. The catalysts conditioned by the present invention cause minimal conversion of $SO_2$ to $SO_3$. The platinum group metal compositions soluble or dispersible in the diesel fuel and are added in amounts effective to provide concentrations of the metal in the fuel of less than 1 part per million (ppm).

14 Claims, No Drawings

OPERATION OF DIESEL ENGINES WITH REDUCED PARTICULATE EMISSION BY UTILIZATION OF PLATINUM GROUP METAL FUEL ADDITIVE AND PASS-THROUGH CATALYTIC OXIDIZER

RELATED APPLICATIONS

This application is a continuation-in-part of copending, commonly-assigned U.S. patent application entitled "Platinum Metal Fuel Additive For Water-Containing Fuels" Ser. No. 08/372,188, filed Jan. 13, 1995 in the names of J. D. Peter-Hoblyn, B. N. Sprague and J. M. Valentine, which application is in turn a continuation-in-part of U.S. patent application entitled "The Reduction of Nitrogen Oxides From Diesel Engines" Ser. No. 08251,520, filed in the names of J. D. Peter-Hoblyn and J. M. Valentine on May 31, 1994, which application is in turn a continuation-in-part of U.S. patent application entitled "The Reduction of Nitrogen Oxides From Vehicular Diesel Engines" Ser. No. 07/918, 679, filed in the name of J. M. Valentine on Jul. 22, 1992. This application is also a continuation-in-part copending, commonly-assigned U.S. patent application entitled "The Reduction of Nitrogen Oxides From Diesel Engines" Ser. No. 08/251,520, filed in the names of J. D. Peter-Hoblyn and J. M. Valentine on May 31, 1994, which application is in turn a continuation-in-part of U.S. patent application entitled "The Reduction of Nitrogen Oxides From Vehicular Diesel Engines" Ser. No. 07/918,679, filed in the name of J. M. Valentine on Jul. 22, 1992. This application is also a continuation-in-part of U.S. patent application entitled "Method for Reducing Harmful Emissions from a Diesel Engine Equipped with a Particulate Trap" Ser. No. 08/003,245 filed Jan. 11, 1993 by J. D. Peter-Hoblyn, W. R. Epperly, and J. M. Valentine, which application is in turn is a continuation-in-part of U.S. patent application having Ser. No. 07/808,435, entitled "Method for Reducing the Particulate Emissions from a Diesel Engine", filed in the names of J. D. Peter-Hoblyn, J. M. Valentine, W. R. Epperly, and B. N. Sprague on Dec. 16, 1991, which in turn is a continuation-in-part of U.S. patent application having Ser. No. 07/794,329 entitled "Method for Reducing Emissions From or Increasing the Utilizable Energy of Fuel for Powering Internal Combustion Engines", filed in the names of W. R. Epperly, B. N. Sprague, D. Kelso, and W. E. Bowers, on Nov. 12, 1991, which in turn is a continuation of U.S. patent application Ser. No. 07/291,245, filed Dec. 28, 1988, now abandoned. The disclosures of each of these prior applications are hereby incorporated by reference in their entireties.

TECHNICAL FIELD

The invention relates to reducing the combined total of particulates, gaseous hydrocarbons and carbon monoxide discharged with the exhaust of diesel engines having having "pass-through catalytic oxidizers", also referred to in the art as "flow-through oxidation catalysts". These flow-through oxidation catalysts are improved according to the invention, initially, by reducing their tendency to oxidize $SO_2$ to $SO_3$ and, over time, by maintaining catalytic activity.

Diesel engines have a number of important advantages over engines of the Otto type. Among them are fuel economy, ease of repair and long life. From the standpoint of emissions, however, they present problems more severe than their spark-ignition counterparts. Emission problems relate to particulates, nitrogen oxides ($NO_x$), unburned hydrocarbons (HC) and carbon monoxide (CO). The particulates themselves have a number of components—each independently troublesome. Particulates comprise a carbon component, a soluble organic fraction (SOF), and $SO_3$. As engine modifications are made to reduce particulates and unburned hydrocarbons, the $NO_x$ emissions increase. Accordingly, some means other than engine modification is needed for new engines and existing engines cannot be easily modified.

Catalytic oxidizers have been proposed to reduce the emission of particulates and gaseous hydrocarbons and carbon monoxide from diesel engines. These devices are primarily intended to oxidize what is referred to as the soluble organic fraction (SOF) of particulates while preferably also oxidizing unburned hydrocarbons and carbon monoxide to reduce emissions of these. Flow-through catalytic oxidizers direct the flow of particulates through a maze of catalyzed surfaces which contact the particulates without either trapping them as done by diesel particulate traps or reducing $NO_x$ the way triple effect catalysts do for gasoline engines.

Catalysts typically employed to reduce particulates and unburned hydrocarbons after combustion, tend to oxidize $SO_2$ to $SO_3$ —thereby converting a benign gaseous component to a form which adheres to the particulates as aqueous sulfuric acid—an unsatisfactory compromise. Additionally, the catalytic surfaces are expensive and rapidly foul.

There is a present need for economical improvements which would permit the use of catalytic devices of the pass-through type to reduce emissions of particulates from diesel engines both initially and over extended periods of operation.

BACKGROUND ART

Diesel engines are used in passenger cars and, to a greater degree, in trucks and buses; however, because of their wide use, their emissions can have a significant, negative environmental impact. Also, even modest uses in enviornments such as mining, can be a problem. Interest is strong in developing means to operate diesel engines while controlling their most troublesome characteristics.

In a July 1994 paper entitled "Particulate Emission Control of Diesel-Fueled Vehicles", B. I. Bertelsen presented a "Status Report" discussing the coming regulations, accomplishments to date and shortcomings of current technology. He notes that the art has developed catalytic oxidizers for diesel engines in the form of traps and pass-through catalysts. Both types of catalytic structures enable operation of the diesel engines with reduced emission of particulates. However, as currently available, neither type can be effective over long periods of operation. The traps become plugged, and it is difficult to remove the particulates they collect. Additionally, the catalysts tend to become inactive for a variety of reasons and tend to oxidize $SO_2$ to $SO_3$. This latter problem also affects catalytic devices of the pass-through type. Increasing precious metal content in an effort to improve durability increases the problem of oxidation of $SO_2$ to $SO_3$.

Diesel particulates, their effect and control, are at the center of much concern and controversy. Their chemistry and environmental impact present complex issues. Very generally, the diesel particulate matter is principally solid particles of carbon and metal compounds with adsorbed hydrocarbons, sulfates and aqueous species. Among the adsorbed species is a soluble organic fraction (SOF) known to contain aldehydes and polycyclic aromatic hydrocarbons (also called PAH's). Some of these organics have been reported to be potential carcinogens. Unburned hydrocarbons are related to the characteristic diesel odor and include aldehydes such as formaldehyde and acrolein. The aldehydes, like the carbon monoxide, are the products of incomplete combustion.

It is not just these organics which are of concern. In one study, diesel particulates were tested along side $TiO_2$ and carbon without any adsorbed hydrocarbons. (U. Heinrich, et al, "Tierexperimentelle Inhalationsstudien Zur Frage der Tumorinduzierenden Wirkung von Dieselmotorabgasen und zwei Teststauben", Oklolgische Forschung BMFT/GSF, Munich, 1992) The reporters determined that all species tested showed carcinogenic tendency. Until further work clarifies this matter, it would be prudent to look for systems which could control particulates of all composition.

Unfortunately, increasing the recovery of particulates by utilizing a trap device, can decrease fuel economy by increasing exhaust back pressure due to particulate buildup within the trap. Moreover, the various pollutants seem to be interrelated, with reduction of one sometimes increasing levels of another. By modifying combustion to achieve more complete oxidation, decreases can be achieved for pollutants resulting from incomplete combustion, but $NO_x$ is typically increased under these conditions.

$NO_x$, principally NO and $NO_2$, contributes to smog, ground level ozone formation and acid rain. NO is produced in large quantities at the high combustion temperatures associated with diesel engines. The $NO_2$ is formed principally by the post oxidation of NO in the diesel exhaust stream. Several attempts have been made to reduce $NO_x$, such as by retarding engine timing, exhaust gas recirculation, and the like; however, with current technology, there is a tradeoff between $NO_x$ and particulates. When $NO_x$ is reduced, particulate emissions increase. And, as noted, conditions favoring low emissions of $NO_x$ often favor production of increased levels of CO and HC. It would be desirable to have a catalyst system which control particulate emissions to a level permitting the use of known means to reduce $NO_x$.

In "A New Generation of Diesel Oxidation Catalysts", Society of Automotive Engineers (SAE Paper No. 922330, 1992), R. Beckman, et al. assert that the technical challenge is to find a catalyst which selectively catalyzes the oxidation of carbonaceous components at low exhaust temperatures typical of diesels operating at partial load, and that does not oxidize sulfur dioxide or nitrogen oxide at high load temperatures. They described tests (without specifically identifying the catalysts) studying the aging of platinum-catalyzed cordierite honeycomb traps, and concluded, inter alia, that the aging was related to adsorption of sulfur and this depended on both the sulfur content of the fuel and the phosphorous content of the lubricating oil. With control of both of these, aging could be slowed. However, sulfur will remain in diesel fuels, even with planned reduction to 0.05%, and there will continue to be a need for a means to maintain the activity of catalysts for reducing emissions of particulates, and preferably also carbon monoxide and unburned hydrocarbons.

In "Control of Diesel Engine Exhaust Emissions in Underground Mining", 2nd U.S. Mine Ventilation Symposium, Reno, Nevada, Sep. 23–25, 1985, at page 637, S. Snider and J. J. Stekar report that precious metal catalysts in a catalytic trap oxidizer and a "catalyzed Corning trap" were effective in the capture of particulate matter, but both systems increased the conversion of $SO_2$ to $SO_3$. The increase in the rate of oxidation of the benign, gaseous dioxide form to the trioxide form results in the adsorption of greater amounts of acid sulfates and associated water onto the discharged particulates, increasing their mass.

The Snider, et al. report also discussed several other approaches, including the use of a fuel additive containing 80 ppm manganese and 20 ppm copper to reduce the regeneration temperature of the trap. While this was effective in reducing the particulate ignition temperature for a trap, this is not a consideration for flow-through oxidizers which do not trap particulates. No measurable reductions in carbon monoxide, unburned hydrocarbons or $NO_x$ were noted.

In a 1987 report, R. W. McCabe and R. M. Sinkevitch summarized their studies of diesel traps catalyzed with platinum and lithium, both individually and in combination. (Oxidation of Diesel Particulates by Catalyzed Wall-Flow Monolith Filters. 2. Regeneration Characteristics of Platinum, Lithium, and Platinum-Lithium Catalyzed Filters; SAE Technical Paper Series-872137) They noted that carbon monoxide conversion to the dioxide was negligible over the lithium filter, good for platinum, but good only initially for the combined catalyst. They further noted that platinum undergoes a reversible inhibition due to the presence of $SO_2$, but in the presence of the lithium catalyst there is apparently a wetting of the platinum crystallites by $Li_2O_2$.

The use of catalysts has taken many forms, but none have been found to be fully ,.satisfactory. While catalysts can be effective in reducing carbon monoxide and unburned hydrocarbons, they are either too easily fouled, have associated health risks, catalyze the oxidation of $SO_2$ to $SO_3$ (which then combines with water and adds to the mass of particulates), or have two more of these shortcomings.

The catalysts will typically be applied to a heat-resistant support and contain a combination of two or more catalyst metals—preferably selected from among platinum group metals such as platinum, palladium, and/or rhodium, transition metals such as cerium, copper, nickel and iron. Unfortunately, the general experience with combinations of catalyst metals, including palladium, platinum, and the even more-expensive rhodium, is that they lose their optimal activity after reasonably short periods of operation. Renewing the catalysts generally entails replacing the unit—an extremely costly undertaking. It would be desirable to simply and inexpensively enable the initial selective catalysis to provide oxidation of hydrocarbons without the formation of $SO_3$ and continued operation for extended service.

While not related to flow-through oxidizers for diesel engines, Dalla Betta, Tsurumi, and Shoji disclose in U.S. Pat. No. 5,258,349, that graded palladium catalysts are sometimes necessary to provide a low light off temperature and avoid hot spots. In U.S. Pat. No. 5,216,875, Kennelly and Farrauto disclose that maintenance of combustion temperature is necessary to avoid inactivation of palladium oxide catalysts.

In addition, the art is replete with teachings that the production of pollutants such as unburned hydrocarbons can cause severe loss of catalytic activity. Also, sulfur and other compounds, such as chlorine, phosphorous, arsenic, lead, and the like, tend to poison or otherwise inactivate catalysts. The above patents and all of the those referred to or cited therein are specifically incorporated by reference in their entireties to show the structure, composition and operation of flow-through oxidation catalysts.

There is a present need for an improved means for rendering the exhaust from diesel engines more environmentally benign, and especially to enable this without the rapid inactivation of expensive catalytic units or the production of harmful byproducts such as increased levels of sulfates. There is a need to enable the operation of a pass-through catalytic oxidizer over long time periods with continued catalytic activity and without excessive conversion of $SO_2$ to $SO_3$.

DISCLOSURE OF INVENTION

It is an object of the invention to provide method for improving the operation of a diesel engine, by enabling the operation of a pass-through oxidation catalyst over long periods of time with continued catalytic activity.

It is another object of the invention to provide method employing a fuel additive to improve the operation of a pass-through oxidation catalyst with continued catalytic activity for the reduction of particulates and gaseous hydrocarbons and carbon monoxide over long periods of time.

It is an object of the invention to provide method for improving the operation of a diesel engine, by enabling the operation of a pass-through oxidation catalyst over long periods of time with continued catalytic activity and without the undesirable conversion of $SO_2$ to $SO_3$.

It is another object of the invention to provide method employing a fuel additive to improve the operation of a pass-through oxidation catalyst with long-term catalytic activity for the reduction of particulates and gaseous hydrocarbons and carbon monoxide, without the undesirable conversion of $SO_2$ to $SO_3$.

The method of the invention comprises: providing a diesel engine including an exhaust system employing a pass-through catalyst support having sufficient surface to support an active oxidation catalyst for oxidizing at least a portion of the particulates discharged from the engine upon operation of the engine; introducing a fuel comprising a platinum group metal composition into a combustion chamber of a diesel engine, said platinum group metal composition being stable in the fuel composition prior to combustion and consumable during combustion to release platinum metal catalyst in active form; combusting the fuel within said combustion chamber to release from the fuel upon combustion an active firm of catalyst to deposit within the pass-through catalyst support to thereby catalyze the support and maintain the catalytic activity thereof.

The pass-through catalyst support can initially be either catalyzed or uncatalyzed, and if catalyzed in any stage of activity. Preferably, the support is fully catalyzed to function as a pass-through catalytic oxidizer, typically capable of removing at least 40%, and preferably at least 60%, of the soluble organic fraction (SOF) of the particulates generated by the operation of the diesel engine, and most preferably to also reduce the level of gaseous unburned hydrocarbons and carbon monoxide by at least 40%. Preferably, the combined weight of particulates and gaseous hydrocarbons and carbon monoxide is reduced by at least 30%. Also, the catalyst should preferably be selective, both initially and as maintained in activity by the invention. By this it is meant a catalytic activity is provided to reduce emissions of particulates, and preferably carbon monoxide and unburned hydrocarbons, but causes minimal conversion of $SO_2$ to $SO_3$.

The platinum group metal compositions are preferably soluble in the diesel fuel and added in amounts effective to provide concentrations of the metal in the fuel of less than 1 part per million (ppm). They can be premixed with the bulk fuel or added to it after fueling either to the fuel tank or in-line from an on-board reservoir The platinum group metal compositions can, however, be simply dispersible in the fuel and can be employed as part of an emulsion, either partly- or wholly-soluble in either a lipophilic or hydrophilic phase as will be explained in more detail below. While not preferred, the platinum group metal compositions can be added to the combustion air. For the purposes of this description, all "parts per million" figures are on a weight to volume basis, i.e., grams/million cubic centimeters (which can also be expressed as milligrams/liter), and percentages are given by weight, unless otherwise indicated.

DETAILED DESCRIPTION OF THE PREFERRED EMBODIMENT

In this description, the term "Diesel engine" is meant to include all compression-ignition engines, for both mobile (including marine) and stationary powerplants and of the two-stroke per cycle, four-stroke per cycle and rotary types.

It is an advantage of the invention that the use of the platinum group metal compound improves the operation of a pass-through oxidation catalyst both by decreasing the loading of pollutants received by it, but also by helping to maintain its catalytic activity with good selectivity. While not wishing to be bound by any particular theory, it is believed that combustion of the diesel fuel is enhanced initially and that oxidation is continued through the exhaust system of a lean-burn diesel engine (e.g., from 2 to about 12% oxygen greater than stoichiometrically required) equipped with a pass-through oxidation catalyst. Preferably, the net effect is to reduce the combined weight of particulates and gaseous hydrocarbons and carbon monoxide by at least 25%, preferably at least 45%, of what that weight would be in the absence of the platinum group metal. The mechanism for the retarding of catalyst inactivation is not fully understood, but is believed to relate to the replenishment of active catalyst on the surfaces of the catalyst support of the pass-through oxidation catalyst.

Pass-through oxidation catalysts are especially designed to reduce the SOF of particulates, and the gaseous components of the exhaust which are the results of incomplete combustion, namely unburned hydrocarbons and carbon monoxide. Unlike traps, the pass-through catalytic oxidizers do not filter out or otherwise trap the particulates. The general construction and operation of these devices are described in the references cited above which are incorporated herein by reference for these teachings.

Flow-through oxidation catalysts are improved, initially, by reducing their tendency to oxidize $SO_2$ to $SO_3$. They are also improved over time by maintaining catalytic activity. The pass-through catalyst support can initially be either catalyzed or uncatalyzed, and if catalyzed in any stage of activity. The nature of these supports is to be receptive to catalytic metals, but they can be specially treated to enhance the reception of active catalyst metal from the exhaust as may be desired.

Preferably, the support is fully catalyzed to function as a pass-through catalytic oxidizer capable of removing at least 60%, and preferably at least 75%, of the SOF of the particulates generated by the operation of the diesel engine, and most preferably to also reduce the level of gaseous unburned hydrocarbons and carbon monoxide by at least 40%. Preferably, the combined weight of particulates and gaseous hydrocarbons and carbon monoxide is reduced by at least 40%. Also, the catalyst should preferably be selective, both initially and as maintained in activity by the invention. By this it is meant a catalytic activity is provided to reduce emissions of particulates, and preferably carbon monoxide and unburned hydrocarbons, but causes minimal conversion of $SO_2$ to $SO_3$.

The platinum group metal compositions, which will be defined in greater detail below, are most preferably added directly to diesel fuels can be "distillate fuels" including diesel fuels meeting the ASTM definition for diesel fuels or others even though they are not wholly comprised of distillates and can comprise alcohols, ethers, organo-nitro compounds and the like (e.g., methanol, ethanol, diethyl ether, methyl ethyl ether, nitromethane), and water in emulsified form. Also within the scope of this invention, are liquid fuels derived from vegetable or mineral sources such as corn, alfalfa, shale, and coal. These fuels may also contain other additives which are well known to those skilled in the art. These can include dyes, cetane improvers, anti-oxidants such as 2,6-di-tertiary-butyl-4-methylphenol, rust inhibitors such as alkylated succinic acids and anhydrides, bacteriostatic agents, gum inhibitors, metal deactivators, upper cylinder lubricants, antiicing agents, demulsifiers and the like.

The effective platinum group catalyst metal compositions are those described by the patents and applications incorporated by reference above. Particularly preferred are platinum group metals in the form of compositions (typically, specific compounds or reaction mixtures) which can be dissolved in or dispersed in the fuel either directly or in an emulsion. These compositions will, upon initiation of combustion release the active form of the catalyst metals. Included specifically, are the petroleum-soluble organometallic platinum group metal coordination compounds discussed in or embraced by U.S. Pat. Nos. 4,891,050 and 4,892,562 to Bowers, et al., U.S. Pat. No. 5,034,020 to Epperly, et al., and U.S. Pat. No. 5,266,093 to Peter-Hoblyn, et al. In addition, the catalyst composition present in the fuel can be comprised of more water-sensitive and even water soluble compounds. A representative listing of these types of compounds is given below. A representative listing of the petroleum-soluble compounds is found in the above cited patents which are hereby incorporated by reference in their entireties.

The preferred fuel for admixture with the additive containing the platinum group metal catalyst composition, e.g., one of the named compounds, is diesel fuel, and the additive containing the catalyst can be added either to the fuel directly or to the lubricating oil in engines, such as two-stroke engines in which the oil is burned along with the fuel. In engines of this type, the oil can be introduced into the cylinders either in mixture with the fuel or separately injected into the engine. When the oil is added as part of the fuel, it will typically be blended at a ratio of from about 1:10 to about 1:75, e.g., from about 1:15 to about 1:25. When added to the fuel, the platinum group metal composition can be supplied as fully mixed with the bulk of the fuel in the principal fuel tank or in concentrated form from an onboard reservoir separate from the principal fuel tank. Additionally, while not particularly preferred, the platinum group metal composition can be added to the combustion air and mixed with the fuel in the combustion chamber. In this latter case, the composition can be added from an on-board reservoir in the same proportion to the fuel as in the other cases.

It is an advantage of the invention that the effective additive catalyst compositions need not be highly fuel-soluble. The effective catalyst compositions can, however, comprise any of the petroleum-soluble organometallic platinum group metal coordination compounds discussed in or embraced by U.S. Pat. Nos. 4,891,050 and 4,892,562 to Bowers, et al., U.S. Pat. No. 5,034,020 to Epperly, et al., and U.S. Pat. No. 5,266,093 to Peter-Hoblyn, et al.

In addition to the highly fuel-soluble compounds taught by the art to be stable in the presence of water, the invention makes possible the use of platinum group metal and other catalyst compounds which would normally be taken up in any water present. These platinum group metal compounds can be either simply water-sensitive or essentially water-soluble. Water-sensitive platinum group metal compounds are characterized as being instable in the presence of from about 0.01 to about 0.5% water, but having sufficient affinity for the fuel that when a water-functional additive is employed in accordance with the invention, they remain in the fuel and effective for their intended catalytic function. The water-sensitive compounds typically have partition ratios of from about less than 50, down to about 1. Compounds of this type having partition ratios as low as 40 and below, e.g., less than 25, and more narrowly less than 1 to 20, can be effective according to the invention. Also, essentially water-soluble platinum group metal compounds having partition ratios of less than 1 can be employed according to the invention.

The fuel additives can include a water-functional composition selected from the group consisting of lipophilic emulsifiers, lipophilic organic compounds in which water is miscible, and mixtures of these. The preferred compounds will have the capability of preventing frank separation of water from the fuel and will preferably maintain it tied up in the fuel, preferably in complete miscibility with a nonpolar fuel component or in droplets no larger than about 2 μ, and preferably smaller than about 1 μ in diameter, based on a weight average of droplet sizes. Discrete pockets or pools of water, where the uniform distribution of the platinum group metal within the fuel is disturbed, are preferably avoided.

In addition to the required components, it is preferred to employ a suitable hydrocarbon diluent such as any of the higher aliphatic alcohols (e.g., having over 3 carbons, i.e., from 3 to 22 carbons), tetrahydrofuran, methyl tertiarybutyl ether (MTBE), octyl nitrate, xylene, mineral spirits or kerosene, in an amount effective to provide a suitably pourable and dispersible mixture. Additionally, where the fuel additive is intended for use in an application where a commercially-available fuel can be expected to contain a demulsifier, then an additional amount of emulsifier specifically intended to overcome the effects of such can be employed. Also, the use of additives known to the art as described above and in the references there cited, can be employed as the application calls for. Specifically, it is sometimes desirable to add one or more of corrosion inhibitors, cetane improvers, octane improvers, lubricity control agents, detergents, antigel compositions, and the like.

The invention is seen to have wide application to gasoline and diesel fuels containing from about 0.01 to about 0.5% water as a contaminant (e.g., tramp water). However, consistent with the objective of controlling the tendency of water to render the platinum group metal compounds inactive, there are instances where the overt addition of water can be beneficial. It is a distinct advantage of the invention that overt addition of water, e.g., from about 1 to about 65%, can be accomplished without rendering the platinum group metal compounds inactive.

For example, fuel mixtures can be prepared as emulsions of diesel fuel and water, as mentioned above, but preferably including from about 5 to about 45% (more narrowly, 10 to 30%) water, for the purpose of controlling the amount of $NO_x$ produced during combustion. These emulsions can include a platinum group metal compound at a level of from about 0.1 to about 1.0% of the weight of the fuel mixture, to reduce the carbon monoxide and hydrocarbon emissions, and employing a lipophilic emulsifier at a ratio of from about 1:10,000 to about 1:500,000 (more narrowly, from about 1:50,000 to about 1:250,000) based on the weight of the platinum.

Also, there are instances wherein the use of complex emulsions (typically including a continuous hydrocarbon phase having dispersed therein droplets of water, which in turn have droplets of a lipophilic fluid dispersed therein). In one exemplary formulation of such a complex emulsion, the droplets of lipophilic fluid as the internally-dispersed phase can comprise the fuel additive, including the platinum group metal and the water-functional composition, e.g., a suitable emulsifier having the capability to maintain an emulsion of this type.

The emulsifiers effective for the complex emulsions will preferably contain a hydrophilic emulsifier such as higher ethoxylated nonyl phenols, salts of alkyl and alkyl ether sulfates, ethoxylated nonyl phenols with higher degrees of ethoxylation, higher polyethylene glycol mono- and di-esters, and higher ethoxylated sorbitan esters (e.g., higher in these contexts means from a lower level of 4–6 to about 10 or more). The fuel additive for use in preparing the complex emulsion preferably comprises a continuous hydrocarbon phase including a hydrophilic emulsifier at a concentration of from about 0.1 to about 10%, and a dispersed phase comprised of aqueous droplets having a platinum group metal compound dissolved or dispersed therein and a lipophilic emulsifier at a concentration of from about 0.1% to about 10% based on the weight of platinum group metal in the additive composition, said lipophilic emulsifier being characterized by oil solubility and water dispersibility.

To better understand the above concept, the following exemplary procedure is presented: (1) The lipophilic emulsifier is added to the oil to be used for the internal phase at a ratio of from about 0.1 to about 10% of the total composition. Platinum group metal compounds may be dissolved or dispersed in this oil as desired. (2) The combined oil/lipophilic emulsifier just described is added to a solution of the hydrophilic emulsifier in water with stirring to form an oil-in-water emulsion. The concentration of hydrophilic emulsifier in the water is also between about 0.1 and 10% of the total composition. Water-soluble or dispersible platinum group metal compounds may be dispersed in the water as needed. (3) The oil-in-water emulsion described in step 2 is then added to oil containing the lipophilic emulsifier at a ratio of 0.1 to 10% of the total composition to form the final oil/water-in-oil emulsion.

Among the lipophilic emulsifiers suitable as the water-functional composition are, preferably, those emulsifiers having an HLB of less than about 10, and more preferably less than about 8. The term "HLB" means "hydrophile-lipophile balance" and is determined, as known from the procedure developed by ICI Americas, Inc. of Wilmington, Delaware, from a test of the relative solubility or dispersibility of the emulsifier in water, with nondispersible being 1–4 and fully dispersible being 13.

The emulsifier can be anionic, nonionic or cationic. Among the preferred anionic emulsifiers are sodium or TEA petroleum sulfonates, sodium dioctyl sulfosuccinates, and ammonium or sodium isostearyol 2-lactylates. Among the preferred cationic emulsifiers are lower ethoxylated amines, oleyl imidazolines and other imidazoline derivatives. Among the preferred nonionic emulsifiers are alkanolamides including oleamide, oleamide DEA, and other similar compounds, lower ethoxylated alkyl phenols, fatty amine oxides, and lower ethoxylated sorbitan esters (e.g., lower in these contexts means from 1 to an upper level of from about 4–6). Functionally, materials meeting the following criteria can be effective individually and in combinations to stabilize the presence of water-sensitive and water-soluble platinum group metal compounds in water-containing systems. Concentrations will be dependent on the exact formulation and the expected water content of the fuel, but concentrations of from about 0.01 to about 5%, based on the weight of the fuel as combusted, and assuming a water concentration of up to about 0.05%, are among those preferred. In some cases, it is more meaningful to express the concentration on the basis of the platinum group metal, and in this case it is preferably at a ratio of from about 10:1 to about 500,000:1 as compared to the weight of platinum group metal in the additive composition.

It is sometimes preferred to employ a combination of emulsifiers, because the various hydrocarbons in the fuels interact differently with the same emulsifier. Often, individual emulsifiers are less effective than combinations due to interactions, including those between the fuel and the emulsifier. One exemplary combination of emulsifiers, referred to herein also as an emulsification system, which can be utilized comprises about 25% to about 85% by weight of an amide, especially an alkanolamide or n-substituted alkyl amine; about 5% to about 25% by weight of a phenolic surfactant; and about 0% to about 40% by weight of a difunctional block polymer terminating in a primary hydroxyl group. More narrowly, the amide can comprise about 45% to about 65% of the emulsification system; the phenolic surfactant about, 5% to about 15%; and the difunctional block polymer, about 30% to about 40% of the emulsification system.

Suitable n-substituted alkyl amines and alkanolamides are those formed by the condensation of, respectively, an alkyl amine and an organic acid or a hydroxyalkyl amine and an organic acid, which is preferably of a length normally associated with fatty acids. They can be mono-, di-, or triethanolamines and include any one or more of the following: oleic diethanolamide, cocamide diethanolamine (DEA), lauramide DEA, polyoxyethylene (POE) cocamide, cocamide monoethanolamine (MEA), POE lauramide DEA, oleamide DEA, linoleamide DEA, stearamide MEA, and oleic triethanolamine, as well as mixtures thereof. Such alkanolamides are commercially available, including those under trade names such as Clindrol 100-0, from Clintwood Chemical Company of Chicago, Ill. Schercomid ODA, from Scher Chemicals, Inc. of Clifton, N.J.; Schercomid SO-A, also from Scher Chemicals, Inc.; Mazamide®, and the Mazamide series from PPG-Mazer Products Corp. of Gurnee, Ill.; the Mackamide series from McIntyre Group, Inc. of University Park, Ill.; and the Witcamide series from Witco Chemical Co. of Houston, Tex.

The phenolic surfactant can be an ethoxylated alkyl phenol such as an ethoxylated nonylphenol or octylphenol. Especially preferred is ethylene oxide nonylphenol, which is available commercially under the tradename Triton N from Union Carbide Corporation of Danbury, Conn. and Igepal CO from Rhone-Poulenc Company of Wilmington, Del.

The block polymer which is an optional element of the emulsification system can comprise a nonionic, difunctional block polymer which terminates in a primary hydroxyl group and has a molecular weight ranging from about 1,000 to above about 15,000. Such polymers are generally considered to be polyoxyalkylene derivatives of propylene glycol and are commercially available under the tradename Pluronic from BASF-Wyandotte Company of Wyandotte, New Jersey. Preferred among these polymers are propylene oxide/ethylene oxide block polymers commercially available as Pluronic 17R1.

The emulsification system should be present at a level which will ensure effective emulsification of the water present, either alone or with a suitable lipophilic organic compound in which water is miscible (to be described in detail later). As an example, the emulsification system can be present at a level of at least about 0.05% by weight of the fuel to do so. Although there is no true upper limit to the amount of the emulsification system which is present, with higher levels leading to greater emulsification and for longer periods, there is generally no need for more than about 5.0% by weight, nor, in fact, more than about 3.0% by weight.

It is also possible to utilize a physical emulsion stabilizer in combination with the emulsification system noted above to maximize the stability of the emulsion. Use of physical stabilizers also provides economic benefits due to their relatively low cost. Although not wishing to be bound by any theory, it is believed that physical stabilizers increase emulsion stability by increasing the viscosity of immiscible phases such that separation of the oil/water interface is retarded. Exemplary of suitable physical stabilizers are waxes, cellulose products, and gums such as whalen gum and xanthan gum.

When utilizing both the emulsification system and physical emulsion stabilizers, the physical stabilizer is present in an amount of about 0.05% to about 5% by weight of the combination of chemical emulsifier and the physical stabilizer. The resulting combination emulsifier/stabilizer can then be used at the same levels noted above for the use of the emulsification system.

The emulsifiers are preferably blended with the platinum group metal compound and the resulting blend is then admixed with the fuel and emulsified. To achieve a stable emulsion, especially when large amounts of water are intended, a suitable mechanical emulsifying apparatus, such as an in-line emulsifying device, can be employed. Preferred emulsion stabilities will be for time periods of from about 10 days at a minimum to about 1 month or more. More preferably, the emulsion will be stable for at least 3 months.

Among the lipophilic organic compounds in which water is miscible, effective according to the invention, will be water-miscible, fuel-soluble compounds such as butanol, butyl cellosolve (ethyleneglycol monobutyl ether), dipropyleneglycol monometyl ether, 2-hexyl hexanol, diacetone alcohol, hexylene glycol, and diisobutyl ketone. Functionally, materials meeting the following criteria can be effective: that they have a water miscibility of at least about 10 g of water per liter of the material, and be soluble in the fuel (when the material contains the 10 g of water) in an amount of about at least 10 g per liter of total fuel. Additionally, the water functional composition will preferably be characterized by hydroxy, ketone, carboxylic acid funtional group, ether linkage, amine group, or other polar functional groups that can serve as water acceptors on a hydrocarbon chain. Concentrations will be dependent on the exact formulation and the expected water content of the fuel, but concentrations of from about 0.01 to about 1.0%, based on the weight of the fuel as combusted, are among those preferred. In some cases, it is more meaningful to express the concentration on the basis of the platinum group metal, and in this case it is preferably at a ratio of from about 1,000:1 to about 500,000:1 relative the weight of platinum group metal in the additive composition.

Platinum group metals include platinum, palladium, rhodium, ruthenium, osmium, and iridium. Compounds including platinum, palladium, and rhodium, especially compounds of platinum alone or possibly in combination with rhodium compounds are preferred on the basis of their relatively high vapor pressures.

Among the effective platinum group metal compounds are any of those effective to release catalytic platinum group metal in the combustion chamber. It is an advantage of the invention that water-soluble platinum group metal compounds, as well as those with varying degrees of solubility in hydrocarbon fuels, can be employed without the presence of water releasing the platinum from the fuel either by precipitation or by plating out on fuel storage or supply surfaces. These include compounds where the platinum group metal exists in oxidation states l and IV.

U.S. Pat. No. 4,891,050 to Bowers, et al., U.S. Pat. No. 5,034,020 to Epperly, et al., and U.S. Pat. No. 5,266,093 to Peter-Hoblyn, et al., describe platinum group metal compounds which are highly-soluble in fuel and have high partition ratios. The entire disclosures of these patents are incorporated herein by reference for their descriptions of suitable platinum group metal compounds and procedures for preparing them. In addition to these materials, are commercially-available or easily-synthesized platinum group metal acetylacetonates, platinum group metal dibenzylidene acetonates, and fatty acid soaps of tetramine platinum metal complexes, e.g., tetramine platinum oleate. In addition, there are the water soluble platinum group metal salts such as chloroplatinic acid, sodium chloroplatinate, potassium chloroplatinate, iron chloroplatinate, magnesium chloroplatinate, manganese chloroplatinate, and cerium chloroplatinate, as well as any of those compounds identified or included within the description set forth by Haney and Sullivan in U.S. Pat. No. 4,629,472.

Typically, the platinum group metal compound will be employed in an amount sufficient to supply the platinum group metal within the range of from about 0.05 to about 2.0 milligrams of platinum group metal per liter of fuel, preferably from about 0.1 to about 1 milligrams of platinum group metal per liter of fuel. A more preferred range is from about 0.10 to about 0.5 milligrams of platinum group metal per liter of fuel. Higher concentrations would be necessary in a concentrate used to dose the fuel at these levels.

Temperature stability of the additive is important in practical and operational terms. Typically, the breakdown temperature of the additive should be at least about 40° C., preferably at least about 50° C., in order to protect against most temperatures to which it can be expected to be exposed. In some circumstances, it will be necessary that the breakdown temperature be no lower than about 75°C.

The additive is also preferably substantially free from objectionable traces of, or functional groups containing, phosphorus, arsenic, and antimony (i.e., they should not contain a substantial amount of such functional groups) which have significant disadvantages like "poisoning" or otherwise reducing the effectiveness of the platinum group metal compound. Preferably, the purified platinum group metal additive compound contains no more than about 500 ppm (on a weight per weight basis) of phosphorus, arsenic, or antimony, more preferably no more than about 250 ppm. Most preferably, the additive contains no phosphorus, arsenic, or antimony.

Compounds including platinum, palladium, and rhodium, especially compounds of platinum alone or with one or more compounds of other catalytic metals are preferred in the practice of this invention.

In alternative embodiments the additives can be employed with other metallic compounds utilized for improving economy, reducing emissions of pollutants such as hydrocarbons and carbon monoxide, and for improving the operation of particulate traps or oxidationcatalysts. Among the useful metallic compounds are salts of manganese, iron, copper, cerium, sodium, lithium and potassium, which can be employed at suitable levels, e.g., from about 1 to about 100 ppm and preferably 30 to 60 ppm of the catalyst metal in combination with the platinum group metal composition in diesel fuels or gasoline. For gasoline engines, the manganese compounds are useful to improve fuel economy. For diesel engines, the manganese, iron, copper, cerium, sodium, and lithium compounds are effective to reduce the ignition temperature of particulates captured in a diesel trap. In combination with the platinum group metals it is possible to significantly reduce carbon monoxide and unburned hydrocarbons while removing particulates more easily from the trap. The above references and those cited therein are incorporated by reference to show specific salts and other compounds of these metals, including the acetonates, proprionylacetonates, and formylacetonates.

Among the suitable lithium and sodium compositions are the salts of lithium and sodium respectively, with suitable organic compounds such as alcohols or acids, e.g., aliphatic, alicyclic and aromatic alcohols and acids. Exemplary of particular salts are the lithium and sodium salts of tertiary butyl alcohol and mixtures of these. Other lithium and sodium organic salts are available and suitable for use to the extent that they are fuel-soluble and are stable in solution. While not preferred, inorganic salts can also be employed to the extent that they can be efficiently dispersed in the fuel, such as in a stable emulsion or otherwise. The specific chemical compounds will be selected to avoid fouling of engine or other parts.

Among the specific sodium compounds are: the salts of sulfonated hydrocarbons, for example sodium petroleum sulfonate, available as Sodium Petronate from Witco Chemical ($NaO_3SR$, R=alkyl, aryl, arylalkyl, and R is a hydrocarbon having greater than three carbons); sodium alcoholates, for example sodium t-butoxide and other fuel- soluble alkoxides (NaOR, wherein R is a lower alkyl, e.g., from 1 to 3 carbons; and sodium napthenate (sodium salts of napthenic acids derived from coal tar and petroleum). Among the specific lithium compounds are the lithium analogs of the above sodium compounds.

Among the specific cerium compounds are: cerium III acetylacetonate, cerium III napthenate, and cerium octoate and other soaps such as stearate, neodecanoate, and octoate (2-ethylhexoate). These cerium compounds are all trivalent compounds meeting the formula: $Ce(OOCR)_3$, wherein R=hydrocarbon.

,Among the specific copper compounds are: copper acetylacetonate, copper napthenate, copper tallate, and soaps like stearate and the like including octoate and neodecanoate. These copper compounds are all divalent compounds, with the soaps meeting the formula: $Cu(OOCR)_2$. In addition, products of copper compounds with various organic substrates to form an organometallic complex as disclosed by Lubrizol patents such as International Publication Number WO 92/20764.

Among the specific iron compounds are: ferrocene, ferric and ferrous acetyl-acetonates, iron soaps like octoate and stearate (commercially available as Fe(III) compounds, usually), iron pentacarbonyl $Fe(CO)_5$, iron napthenate, and iron tallate.

Among the specific managanese compounds are: methylcyclopentadienyl manganese tricarbonyl ($CH_3C_5H_4$ MN $(CO)_3$, as described for example in U.S. Pat. No. 4,191,536 to Niebylski; manganese acetylacetonate, II and III valent; soaps including neodecanoate, stearate, tallate, napthenate and octoate.

The above description is for the purpose of teaching the person of ordinary skill in the art how to practice the present invention, and it is not intended to detail all of those obvious modifications and variations of it which will become apparent to the skilled worker upon reading the description. It is intended, however, that all such obvious modifications and variations be included within the scope of the present invention which is defined by the following claims. For conciseness, several conventions have been employed with regard to listings of chemicals and ranges. The listings of chemical entities throughout this description are meant to be representative and are not intended to exclude equivalent materials, precursors or active species. Also, each of the ranges is intended to include, specifically, each integer, in the case of numerical ranges, and each species, in the case of chemical formulae, which is encompassed within the range. The claims are meant to cover the claimed components and steps in any sequence which is effective to meet the objectives there intended, unless the context specifically indicates the contrary.

We claim:

1. A method for improving the operation of a diesel engine, by enabling the operation of a pass-through oxidation catalyst over long periods of time with continued catalytic activity and without the undesirable conversion of $SO_2$ to $SO_3$, comprising:

providing a diesel engine including a combustion chamber, for combusting a diesel fuel and thereby produce combustion gases including particulates, and an exhaust system, for removing combustion gases from the combustion chamber, said exhaust system including a pass-through catalyst support having sufficient surface to support an active oxidation catalyst for oxidizing at least a portion of the particulates discharged from the engine upon operation of the engine;

introducing a fuel comprising a platinum group metal composition into a combustion chamber of a diesel engine, said platinum group metal composition being stable in the fuel composition prior to combustion and consumable during combustion to release platinum metal catalyst in active form; and combusting the fuel within said combustion chamber to release from the fuel upon combustion an active form of catalyst;

discharging the exhaust from the combustion chamber and passing it through the pass-through catalyst support to deposit the active form of the catalyst within the pass-through catalyst support to thereby catalyze the support for selective catalytic activity.

2. A method according to claim 1 wherein the pass-through catalyst support is intially catalyzed.

3. A method according to claim 1 wherein the pass-through catalyst support is intially uncatalyzed.

4. A method according to claim 1 wherein the pass-through catalyst support is catalyzed by the active metal catalyst in the exhaust effectively to maintain an activity capable of removing at least 25% of the soluble organic fraction of the particulates generated by the operation of the diesel engine.

5. A method according to claim 4 wherein the pass-through catalyst support is catalyzed by the active metal catalyst in the exhaust effectively to maintain an activity capable of reducing the level of gaseous unburned hydrocarbons and carbon monoxide by at least 40%.

6. A method according to claim 4 wherein the pass-through catalyst support is catalyzed by the active metal catalyst in the exhaust effectively to reduce conversion of $SO_2$ to $SO_3$ by 50%.

7. A method according to claim 1 wherein the platinum group metal composition comprises a compound soluble in the diesel fuel and is added in amounts effective to provide concentrations of the metal in the fuel of less than 1 part per million (ppm).

8. A method according to claim 1 wherein the platinum group metal composition comprises a compound dispersible in the fuel with an emulsified aqueous phase, said platinum group metal composition being added in amounts effective to provide concentrations of the metal in the fuel of less than 1 part per million (ppm).

9. A method according to claim 1 wherein the diesel engine is a lean-burn diesel engine operating with from 2 to about 12% oxygen greater than stoichiometrically required.

10. A method according to claim 1 wherein the use of the platinum group metal composition and the pass-through oxidation catalyst is effective to reduce the combined weight of particulates and gaseous hydrocarbons and carbon monoxide by at least 25%, of what that weight would be in the absence of the platinum group metal.

11. A method according to claim 10 wherein the use of the platinum group metal composition and the pass-through oxidation catalyst is effective to reduce the combined weight of particulates and gaseous hydrocarbons and carbon monoxide by at least 45%.

12. A method according to claim 11 wherein the platinum group metal composition is supplied from an onboard reservoir separate from the principal fuel tank.

13. A method according to claim 1 wherein the support is treated to enhance its receptivity to the active catalytic metal in the exhaust.

14. A method for operating of a diesel engine with reduced emission of particulates and gaseous pollutants, comprising:

providing a diesel engine including a combustion chamber, for combusting a diesel fuel and thereby produce combustion gases including particulates, and an exhaust system, for removing combustion gases from the combustion chamber, said exhaust system including a pass-through catalyst support having sufficient surface to support an active oxidation catalyst for oxidizing at least a portion of the particulates discharged from the engine upon operation of the engine;

introducing a fuel comprising a platinum group metal composition into a combustion chamber of a diesel engine, said platinum group metal composition being stable in the fuel composition prior to combustion and consumable during combustion to release platinum metal catalyst in active form; and combusting the fuel within said combustion chamber to improve combustion by reducing the levels of particulates, hydrocarbons, and carbon monoxide and releasing from the fuel upon combustion an active form of catalyst;

discharging the exhaust from the combustion chamber and passing it through the pass-through catalyst support to deposit the active form of the catalyst within the pass-through catalyst support to thereby catalyze the support for selective catalytic activity and to further reduce particulates, carbon monoxide and hydrocarbons in the fuel by oxidation due to contact with the catalyst.

* * * * *